United States Patent [19]
McCurley

[11] Patent Number: 5,158,541
[45] Date of Patent: Oct. 27, 1992

[54] MASTECTOMY COMPRESSION SURGICAL BRASSIERE

[76] Inventor: Arlene B. McCurley, 2339 Foster La., Westlake, La. 70669

[21] Appl. No.: 824,433

[22] Filed: Jan. 23, 1992

[51] Int. Cl.$^5$ .................. A61F 13/00; A61F 15/00
[52] U.S. Cl. .................................. 602/79; 602/53; 602/61; 606/201; 450/55
[58] Field of Search ..................... 602/79, 61, 53; 606/201; 623/7; 450/55, 60, 63

[56] References Cited

U.S. PATENT DOCUMENTS

| | | | |
|---|---|---|---|
| 2,672,612 | 3/1954 | Vale et al. | 450/55 |
| 3,094,125 | 6/1963 | Lewis. | |
| 3,561,442 | 2/1971 | Goswitz. | |
| 3,651,522 | 3/1972 | Bernfeld. | |
| 3,701,168 | 10/1972 | Balow. | |
| 3,795,921 | 3/1974 | Zucker. | |
| 3,896,506 | 7/1975 | Hankin et al. | |
| 3,950,792 | 4/1976 | Williams. | |
| 3,957,057 | 5/1976 | Farino. | |
| 3,968,803 | 7/1976 | Hyman. | |
| 4,023,575 | 5/1977 | Nixon. | |
| 4,024,876 | 5/1977 | Penrock. | |
| 4,185,332 | 1/1980 | Jahnig. | |
| 4,338,946 | 7/1982 | Donnelly. | |
| 4,363,144 | 12/1982 | Goad. | |
| 4,369,792 | 1/1983 | Miller. | |
| 4,828,559 | 5/1989 | Greenberg. | |

*Primary Examiner*—Paul Prebilic
*Attorney, Agent, or Firm*—A. Robert Theibault

[57] ABSTRACT

The present disclosure is directed to a mastectomy compression surgical brassiere having as a component a mastectomy brassiere having a pair of camisole shoulder straps and lined brassiere cups, a rectangular compression pad sewn to the inside of the front of the brassiere at substantially its mid point, the rectangular compression pad is covered with a soft porous VELCRO pile looped structure on its external surface lined with a soft fabric, and has an elastic return force band having a portion of a VELCRO hook fabric fastener fabric secured on the side of said return force band away from the body of said compression pad adapted to engage the loops of the VELCRO pile structure cover on said compression pad to retain surgical gauze pads against the incision between the body and the compression pad, and wherein a loop fabric type hook and fastener fabric is secured to the elastic return force band positioned to attach the VELCRO hooks on the return force band to said brassiere to retain the compression pad of the brassiere and surgical dressing pads firmly in place against a mastectomy incision, and to maintain the brassiere firmy against the body of the wearer.

7 Claims, 2 Drawing Sheets

MASTECTOMY COMPRESSION SURGICAL BRASSIERE

TECHNICAL FIELD

The present invention is directed to the technical field of a brassiere for retaining surgical dressings post operatively over a mastectomy incision area under proper compression.

BACKGROUND OF THE INVENTION

The invention is directed to a brassiere structure which may be placed on the patient immediately following surgery while still in the operating room to retain the surgical compress pads against the incision and properly retain the pads against the incision line at the pressure necessary to promote healing and to eliminate a body wrap or bandage and to eliminate tape burns associated with the use of adhesive tape to retain the surgical gauze pads in place. This is attained by employing an elastic return force band in place with fabric VELCRO fasteners so that as healing progresses the pressure of the brassiere against the incision may be applied as physician desires.

The invention is an integral part of a brassiere structure. It is composed of a mastectomy brassiere, a compression pad and an elastic band to supply the return force needed for compression over the incision. The invention eliminates the need for a body wrap bandage or other bandage associated with adhesive tape and the related tape burns. A consistent and even compression is applied to the incision for 24 hours a day. The compression is applied by an elastic return force band with hook fabric fastener on each end. Compression applied by bandage and tape is inconsistent and uneven because gauze stretches after the first day. Consistent even compression is advantageous to healing and relieving pain.

The elastic band is attached to the left or right side of the back side of the brassiere, near the metal hook and eye assembly, with loop and hook fabric fasteners. The arm on the side of the body opposite the mastectomy is placed through the strap, the normal breast is placed in brassiere cup, the elastic band is brought around the patient's body. Sterile gauze pads are laid over the incision. The compression pad is laid over the gauze and held in place while the compression pad is laid over gauze pads, the return force elastic band is stretched up and over the compression pad and fastened at center of pad near point at which pad is attached to brassiere.

The invention is usually worn 6 to 8 weeks as determined by physician. The compression remains at the same level of intensity for 24 hours a day until physician directs a change.

| | | | |
|---|---|---|---|
| 3,094,125 | Lewis | 3,968,803 | Hyman |
| 3,561,442 | Goswitz | 4,023,575 | Nixon |
| 3,651,522 | Bernfeld | 4,024,876 | Penrock |
| 3,701,168 | Balow | 4,185,332 | Jahnig |
| 3,795,921 | Zucker | 4,338,946 | Donnelly |
| 3,896,506 | Hankin, et al | 4,363,144 | Goad |
| 3,950,792 | Williams | 4,369,792 | Miller |
| 3,957,057 | Farino | 4,828,559 | Greenberg |

The above listed patents disclose either post surgical chest bandages or breast prothesis, with or without accompanying brassieres. They differ from my invention structurally and in the manner in which they function.

A soft compression pad is attached to the inside front of a mastectomy brassiere; the compression pad has an elastic return force band for encircling the body of the wearer, complemental VELCRO hook and loop fasteners, one attached at each end of said return force elastic band on opposite sides of band to hold compression pad in place on the wearer after surgery for comfort and relief of pain, a hook and eye on the brassiere holds brassiere in place over the band and compression pad.

The present invention is directed to a mastectomy compression surgical brassiere for retaining dressing such as surgical compress gauze pads over the incision lines of a single or double mastectomy. The present brassiere is not designed to be a brassiere to hold a prosthesis but to hold a compression pad, to be positioned over gauze pads placed over the incision line of the mastectomy to retain the gauze pads against the incision line of a single or double mastectomy and to eliminate the use of adhesive tapes which are not only discomforting to the patient but which may produce tape burns and which complicates the changing of dressings.

The present invention employs in combination with a mastectomy brassiere, a relatively wide compression pad for a mastectomy which is secured by an elastic band with VELCRO fasteners to permit the patient to change her own surgical dressings since the closure connection and regulation of the pressure exerted upon the gauze pads and the incision is in the front of the brassiere and may be viewed and observed by the wearer.

Other objects and advantages will appear in the course of the following description.

The drawings illustrate the best mode presently known to the inventor for carrying out the invention.

A soft wide compression pad long enough to cover the axilla is attached to the inside center seam of the brassiere. The compression supplied by the pad covers the entire incision area. This compression reduces the severe numbness of the incision near the top of the surgical area, and pain in axilla area, and provides comfort for normal breast, making breathing less difficult and sleep greatly improves.

The brassiere rides on top of the compression pad and the elastic band. The incision is touched only by the soft compression pad.

The metal hook and eye assembly is hooked to fasten the brassiere in the usual manner at back of brassiere.

The present invention is further directed to a mastectomy compression surgical brassiere for providing even consistent compression over the entire length of the incision to enhance healing, provide comfort and improve psychological health, the surgical brassiere will eliminate the body wrap and other bandage of tape and gauze.

The gauze pads are held in place by the compression bandage and are usually discontinued after one week.

The present invention further employs in combination with a mastectomy brassiere for a single mastectomy a compression pad which may be flipped to the right or left side of the body to cover the incision. The hook fastener fabric is on opposite side of the band allowing one brassiere to be used for left or right mastectomy.

The patient will be able to apply the mastectomy compression brassiere without assistance as soon as the arm on the mastectomy side is mobile. After four weeks minimum assistance is needed to reach around the back and attach the elastic band, applying brassiere is simple.

Comfort is built into the brassiere by careful selection of the materials.

The advantages to physicians include time saved the patient visits office less frequent, bandage expense less and confidence in goals set for patient being met.

DESCRIPTION OF THE FIGURES OF DRAWINGS

DESCRIPTION OF THE PREFERRED EMBODIMENTS OF THE INVENTION

Figure 1:
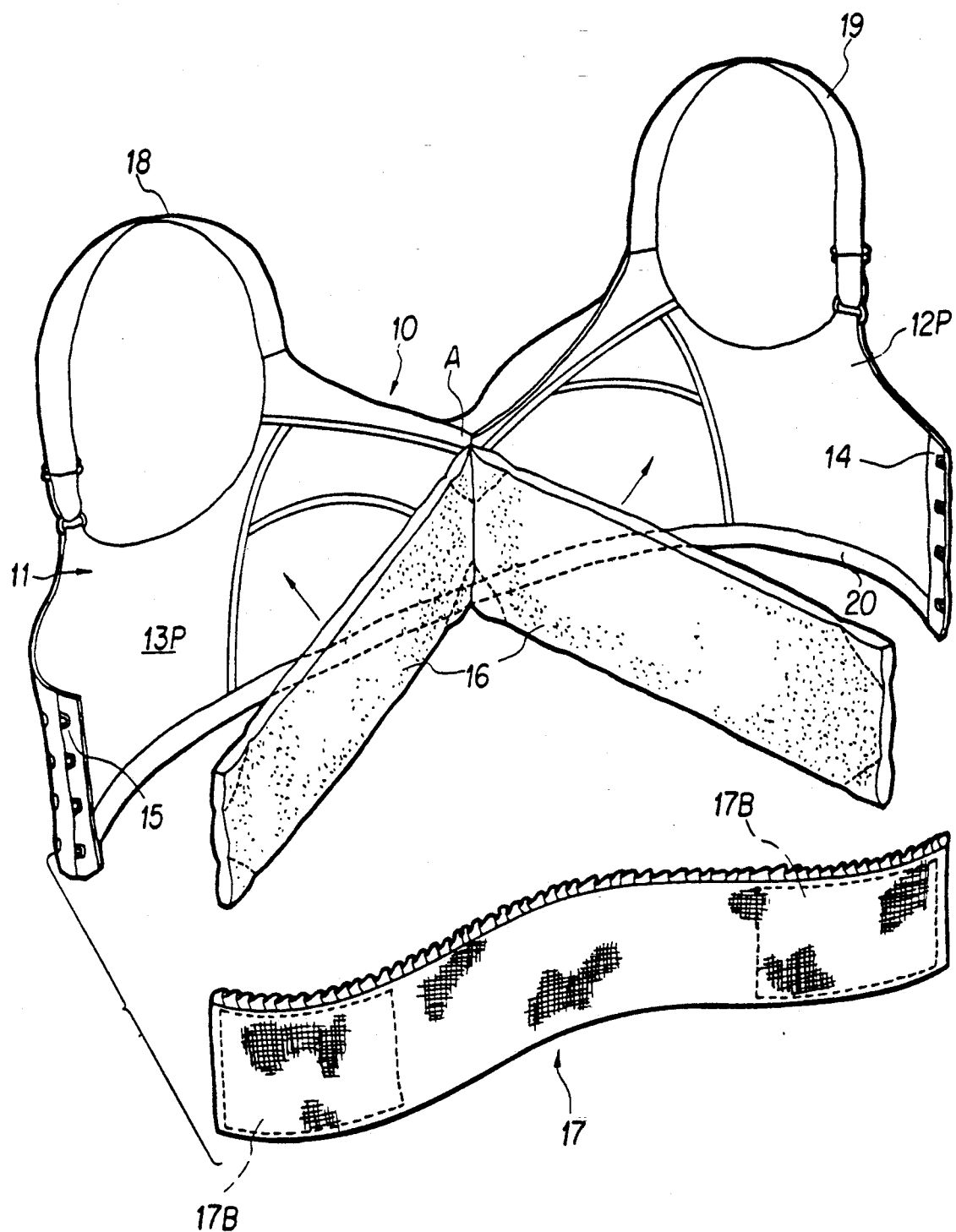
FIG. 1 is a perspective view of the present invention intended for application following a double mastectomy.

Referring now to the drawings and for the moment to FIG. 1 the double mastectomy compression surgical brassiere 10 will be described in which a mastectomy brassiere 10 is shown as having right and left breast cups with lining for future prothesis and having right and left wing panels 12P, 13P terminating at about mid back of the patient in a VELCRO or hook and eye fastener arrangement 14, 15.

Figure 2:
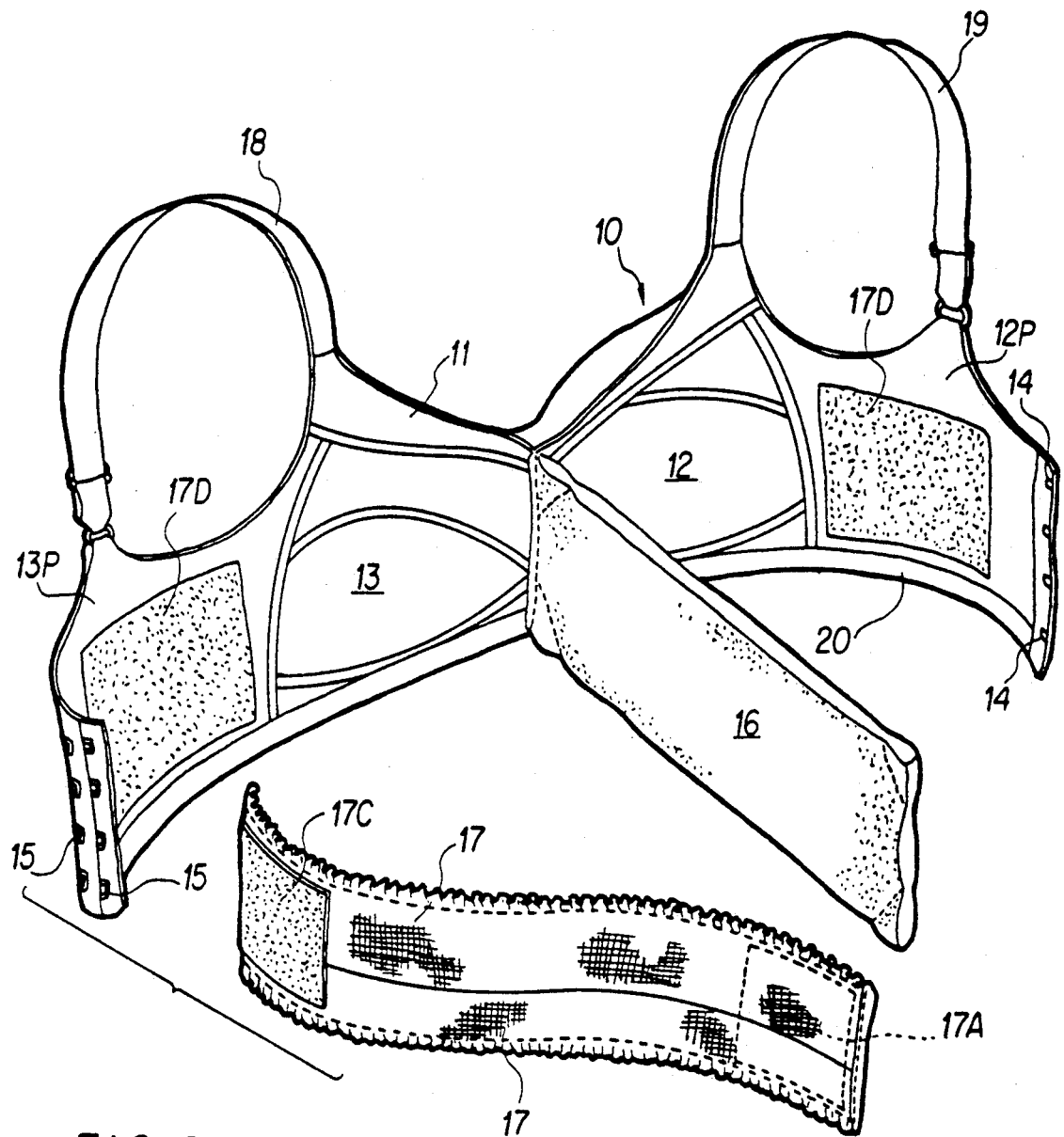
FIG. 2 is a view similar to FIG. 1 showing adaptation of my brassiere to a single mastectomy.

As shown in FIG. 2, 10 designates a mastectomy brassiere having a lined breast covering garment attached to a pair of breast cups 12 and 13 on the front side, a pair of elastic wing panels 12P and 13P terminating in a pair of VELCRO fasteners or metal hook and eyelet fasteners 14 and 15. A compression pad 16 is necessary to retain surgical gauze pads in place to overlie the mastectomy incision and to apply a compression which is sufficient to maintain the gauze pads in place. It had to be covered with a washable material which was comfortable and durable. The pad 16 is covered with a soft non-irritating fabric on its body contacting side and soft loop VELCRO fabric on the back. A soft VELCRO loop fabric covers the entire back side of the foam pad 16. This provided more consistent compression of the compression pad 16 against the incision and gauze pads. This provides a compression pad 16 which is sewn to the back side of the center front seam of the brassiere with the soft fabric side directed toward and held in place against the body of the patient. It provides consistent adequate 24 hour pressure over the incision and axilla, while achieving the desired patient comfort eliminating the body bandage and adhesive tapes and holds sterile gauze pads in place for the time the physician decides to use them. It is easily and quickly applied. The compression pad is rectangular, foam filled, and surged to prohibit shifting of the foam within the lining.

An elastic return force band 17 is used to supply a return force over the compression pad 16 and to retain the surgical gauze pads in place over the incision providing compression to the incision area.

A compression pad 16 is attached to the back side of the center seam of brassiere A, with the soft fabric side toward the body of the wearer. The compression pad 16 meets the following requirements: It provides consistent, adequate 24 hour pressure over the incision and axilla, eliminates body bandage, holds sterile gauze pads in place for the time physician decides to use them, is easily and quickly applied.

An elastic band 17 is used to supply a return force over the compression pad. The requirements met by this second component were: Proper width of band, proper length to supply adequate compression, proper placement on inside of brassiere for the greatest comfort, effectiveness, durability and length and thickness of elastic.

An elastic band four inches wide and cut the appropriate length for brassiere size worn, has hook VELCRO 17A and 17C opposite sides at each end of the band.

Referring now to FIG. 1, the double mastectomy form of my brassiere where the return force band 17 is passed behind the back of the wearer and the VELCRO hooks 17B are secured to the loops of the distal sides of pad 16.

Figure 3:
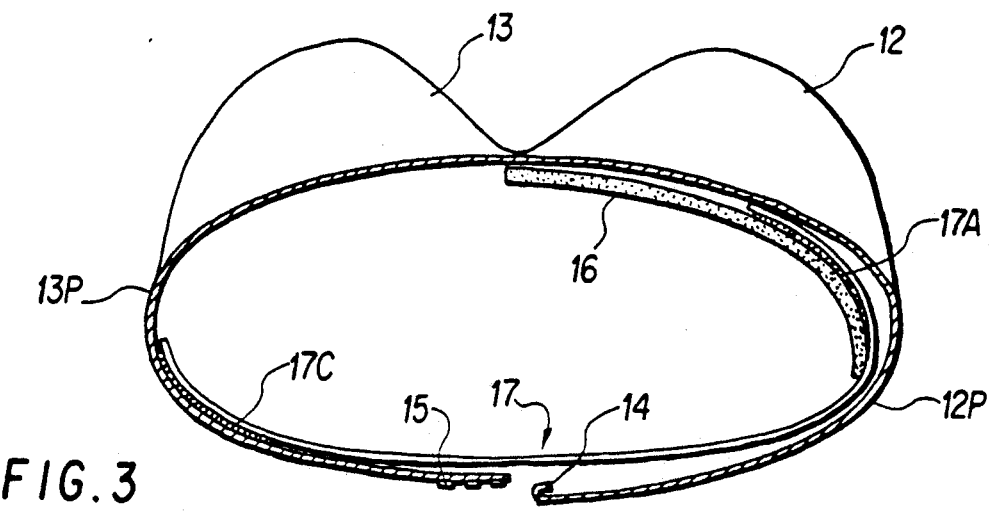
FIG. 3 is a top plan view similar to FIGS. 1 and 2 showing adaptation of my brassiere to a right side mastectomy.

The single mastectomy, as shown in FIGS. 2 and 3, the elastic return force band is attached to the brassiere on the left side, by hook panel 17C to loop panel 17D. The return force band is passed about the wearers back and hook panel 17A is secured to the distal side of pad 16, best seen in FIG. 3, the brassiere is then secured in the back with the usual hook and eye fasteners 14, 15.

For a left side mastectomy the positions of the components are mirrored from those shown in FIG. 3.

One specie of my invention is directed to a mastectomy compression surgical brassiere for use with a single mastectomy (right or left) to be applied to the patient while in the operating room immediately following the operation to take the place of a body bandage.

A single cup of the brassiere will provide support for the retained breast. The elastic band will hold surgical compresses against the mastectomy incision without the need of adhesive tape and its attendant problems. This is shown in FIGS. 2 and 3. The structure of FIG. 3 is employed where the right breast has been removed.

What is common about the structure of FIGS. 2 and 3 is that the compression pad 16 is secured at one end to the inside center of the brassiere. An elastic band 17 is used to supply a return force over the compression pad 16. The return force band 17 is secured to the brassiere by VELCRO fasteners 17C and 17A secured to band 17. 17D is secured to inside of wing panel 12P and 13P.

Adjustable elastic shoulder straps 18, 19 are secured at each end of the brassiere 10 which pass over the shoulder of the wearer to position the brassiere 10 on the body of the patient.

The surgical brassiere is designed so that the brassiere rides on top of the elastic band 17 which supplies the return force and on top of the compression pad. The soft cover of the pad 16 lays next to the chest of the wearer.

The amount of compression applied to the surgical area can be adjusted by the surgeon. The compression is changed by adjusting the VELCRO connection of the movable return force elastic band 17 on top of the compression pad. It can be moved left or right across the pad (parallel to the ground). Both components are fastened by fabric type hook and loop fasteners of the VELCRO type.

The features sought in the brassiere to hold the two major components were:
 (a) A strong fabric on the back of the brassiere (elastic)
 (b) The width of center seam of the order of three and one-half (3½) to three and three-fourth (3¾) inches,
 (c) The width at back near straps should be of the order of three (3) to three and one-half (3½) inches.

(d) No stays are to be employed. The fabric for the brassiere cups is to be cool but supportive.

(e) Camisole straps 18, 19 with adjustment in the back by hook and eye metal or plastic or VELCRO fasteners may be employed.

The widths in the brassiere are to be dictated by the two components of the surgical brassiere, varied to fit brassiere size.

Normal breast comfort for the remaining breast is essential. The brassiere cup is to be lined with a fabric which gives support and is cool to avoid skin irritation caused by twenty-four hour use.

Elastic camisole straps 18, 19 were chosen to avoid using a buckle being near the top of the mastectomy incision area. Many women experience pain in a spot where a buckle is usually placed.

Fleeced no roll, wide; easy stretch elastic 20 is employed at the bottom of the brassiere for comfort.

The post surgical mastectomy brassiere may be put on a patient immediately following surgery. The normal breast is placed in a proper cup after the arm on this side is placed through the strap. The elastic return force band 17 is passed around back of the body to the opposite side. Sterile gauze pads are placed over incision. The compression pad is laid over gauze pads. The compression pad is held in place and the stretch band is brought around the body above the compression pad to the position next to center of brassiere. Press the elastic band to compression pad. The gauze pads are held in place by the movable return force elastic band on top of the compression pad. The compression pad should come to top of arm hole to be in proper position. Place arm in strap on mastectomy side. Hook brassiere in back.

To apply double mastectomy brassiere place return force band under patients back; with hook VELCRO on each end facing up. Lay brassiere across patients chest, fold each half of brassiere to center of the compression pad. The pad is placed in center of chest with soft fabric side next to body. Lift one pad and place gauze pads over half of incision. Lay compression pad on top of gauze pads. Hold in place while elastic band is brought around chosen side and fastened to top of compression pad at center. Repeat procedure for other part of incision. Place arms one at a time in straps. Roll patient to one side and fasten brassiere in back.

What I claim is:

1. A mastectomy compression surgical brassiere for retaining surgical compress gauze pads over a mastectomy incision area comprising a pair of right and left brassiere cups, an at least partially lined compression pad secured at its mid point to an inner side of the brassiere at a center point thereof, said lining of the compression pad comprising looped fabric, an elastic band having hook fabric fastener panels thereon on both ends of the elastic band, said hook fabric fasteners adapted to engage the looped fabric of said compression pad, said elastic band sized to have the hook fastener panels thereof secured to the loop fabric of the compression pads and said loop fabric fastener panels positioned to receive the hooks of said hook fabric fastener panel of said elastic band so that the compression pad is held firmly against the mastectomy incision area.

2. The mastectomy compression surgical brassiere as claimed in claim 1, further comprising a pair of camisole shoulder straps.

3. A mastectomy compression surgical brassiere for retaining surgical compress gauze pads over a mastectomy incision area comprising a pair of right and left brassiere cups, a rectangular compression pad sewn at one of its ends to an inner side of the brassiere at a center thereof to permit the compression pad to be swung over either the right or left brassiere cup to maintain healing pressure against the surgical compress gauze pads over the mastectomy incision area, said compression pad being covered with a lining of soft looped fabric, an elastic band having hook fabric fastener panels thereon on the ends of the elastic band, said hook fabric fasteners adapted to engage the looped fabric of said compression pad, and a looped fabric panel on the brassiere adjacent the brassiere cups which is positioned to receive the hooks of said hook fabric fastener panel of said elastic band so that the compression pad is held firmly against the mastectomy incision area.

4. The mastectomy compression surgical brassiere as claimed in claim 3, further comprising a hook and eyelet assembly for fastening the brassiere to the mastectomy incision area of a patient.

5. The mastectomy compression surgical brassiere as claimed in claim 1, wherein the compression pad is rectangular, foam filled, and surged to prohibit shifting of the foam within the lining.

6. A mastectomy compression surgical brassiere for retaining surgical compress gauze pads over mastectomy incision area comprising a pair of right and left brassiere cups, a rectangular compression pad secured at one of its ends to an inner side of the brassiere to maintain healing pressure against the surgical compress gauze pads over the mastectomy incision area, said compression pad being covered with a lining of soft looped fabric, an elastic band having hook fabric fastener panels thereon on the ends of the elastic band, said hook fabric fasteners adapted to engage the looped fabric of said compression pad, a looped fabric panel on the brassiere adjacent the brassiere cups and positioned to receive the hooks of said hook fabric fastener panel of said elastic band so that the compression pad is held firmly against the mastectomy incision area.

7. The mastectomy compression surgical brassiere as claimed in claim 6, wherein the compression pad is secured at one of its ends to a center of said brassiere.

* * * * *